(12) United States Patent
Knuffman et al.

(10) Patent No.: US 8,350,556 B2
(45) Date of Patent: Jan. 8, 2013

(54) INTEGRATED OPTICAL ELEMENT AND FARADAY CUP

(75) Inventors: Brenton J. Knuffman, Montgomery Village, MD (US); Adam V. Steele, Rockville, MD (US); Jabez J. McClelland, Bethesda, MD (US)

(73) Assignee: The United States of America as represented by the Secretary of Commerce, NIST, Washington, DC (US)

( * ) Notice: Subject to any disclaimer, the term of this patent is extended or adjusted under 35 U.S.C. 154(b) by 396 days.

(21) Appl. No.: 12/691,256

(22) Filed: Jan. 21, 2010

(65) Prior Publication Data

US 2010/0141236 A1 Jun. 10, 2010

(51) Int. Cl.
*G01N 27/62* (2006.01)
(52) U.S. Cl. ........................ 324/71.3; 324/71.1
(58) Field of Classification Search ................. 324/71.1, 324/464, 459
See application file for complete search history.

(56) References Cited

U.S. PATENT DOCUMENTS

| | | | |
|---|---|---|---|
| 6,927,851 B2 | 8/2005 | Mccaffrey et al. | |
| 7,525,736 B2 | 4/2009 | Kuiper et al. | |
| 2001/0038450 A1 | 11/2001 | Mccaffrey et al. | |
| 2002/0014407 A1* | 2/2002 | Allen et al. | 204/298.36 |
| 2002/0070738 A1* | 6/2002 | Yamada et al. | 324/751 |
| 2002/0146200 A1 | 10/2002 | Kudrle et al. | |
| 2007/0206292 A1 | 9/2007 | Kuiper et al. | |
| 2008/0296483 A1 | 12/2008 | McClelland et al. | |
| 2009/0174948 A1 | 7/2009 | Kuiper et al. | |

* cited by examiner

*Primary Examiner* — Vincent Q Nguyen
(74) *Attorney, Agent, or Firm* — Daphne L. Burton; Burton IP Law Group (57) ABSTRACT

An integrated optical element and Faraday cup that can measure charged particle beam currents, manipulate light and analyze charged particle beam energy distribution. One boundary of the cup is formed by a lens or other suitable optical element which can be used for manipulating light along the axis of the Faraday cup. The surface of the optical element interior to the cup is coated with a transparent conductor in order to establish the simultaneous functions of taking charged particle beam current measurements, taking energy distribution measurements and manipulating light for such applications as focusing or imaging. A suppressor/blanker/retarder electrode is designed to eliminate spurious current signals that can result from production of secondary electrons by the charged particle beam impinging on the electrode surface.

17 Claims, 7 Drawing Sheets

INTEGRATED OPTICAL ELEMENT AND FARADAY CUP

STATEMENT REGARDING FEDERALLY SPONSORED RESEARCH/DEVELOPMENT

The subject matter of this patent application was invented by employees of the United States Government. Accordingly, the United States Government may manufacture and use the invention for governmental purposes without the payment of any royalties.

BACKGROUND OF THE INVENTION

1. Field of Invention

The present disclosure relates to Faraday cups used for measuring current in a beam of charged particles and, more particularly, to an integrated Faraday cup and optical element that can measure not only charged particle beam currents and longitudinal energy spread via retarding field energy analysis, but can also manipulate and transmit light.

2. Description of Related Art

Faraday cups may be used to measure current in a beam of charged particles. A Faraday cup may include a conducting metallic enclosure or cup that captures a charged particle beam in a vacuum. An electrical connection between the Faraday cup and a measuring instrument may relay the current to the measuring instrument. Because the charged particle beam current may be very small, a grounded picoammeter may be a suitable choice for current measurement. In addition, steps may also be taken to stop or reduce secondary emissions from distorting the current measurement. Such potentially distortive emissions include secondary electron emissions.

An optical element may comprise one or more optical elements designed to transmit or manipulate light. Faraday cups and optical elements or systems are incompatible. Faraday cups are designed to measure charged particle beam currents, and are not generally designed to transmit light or manipulate light. Unlike Faraday cups, optical elements or systems are designed to manipulate and/or transmit light. Because Faraday cups are not designed for light manipulation or transmission, optical applications may not be enabled on an axis that passes through a Faraday cup.

Unlike Faraday cups, optical elements are not usually designed to measure charged particle beam currents or transmit charged particles. Optical elements are typically manufactured using optically transparent materials which are typically insulating and, therefore, incompatible with charged particles. Accordingly, charged particle beam current measurements may not be enabled along the axis of an optical system. Optical elements are generally involved in generating, propagating, and detecting electromagnetic radiation having wavelengths within a range between the wavelengths of x-rays and microwaves.

In some situations, it may be desirable to simultaneously measure beam current and manipulate light along the same spatial axis. Such dual capabilities or functionalities may be particularly useful for certain applications, such as those that incorporate magneto-optical trap based ion sources (MOTIS). The charged particle source in a MOTIS is a laser-cooled collection of atoms called a magneto-optical trap (MOT). Charged particles, including ions and electrons, may be created in the MOTIS by photo-ionizing atoms in the MOT. These charged particles may be removed from the location of the MOT along an axis defined by an applied electrical field. Along this axis, ions and electrons may be emitted in opposite directions. Charged particle beam current measurements may be taken along this axis.

Because there is a one-to-one correspondence between the number of electrons and ions emitted in a MOTIS, the ion beam current can be determined by measuring the electron beam current. Thus, runtime monitoring of the ion beam current is possible without interrupting the operation of the ion beam. This functionality could be used to generate a control signal for feedback to enhance the stability of beam current. The axis defined by the electrical field is also very convenient for high numerical aperture optical imaging of the MOT. Also, by focusing the photo-ionization laser along this axis, the MOTIS can be operated in a "high-current" mode which may be particularly useful for creating small ion beam sources.

There is a need for a device that integrates the functionalities of a Faraday cup and optical elements by permitting the dual capabilities of beam current measurement, and light manipulation along the same spatial axis.

At times, it may be desirable to measure the energy spread or distribution of a charged particle beam. Energy spread measurements in a charged particle beam may be helpful in a number of ways. For example, energy spread measurements may assist in determining the effects of chromatic aberration of a given ion optical system.

There is a need for a device that integrates the functionalities of a Faraday cup and optical elements by permitting beam current measurement, retarding field energy analysis and light manipulation along the same spatial axis.

BRIEF SUMMARY OF DISCLOSURE

The present disclosure addresses the foregoing deficiencies of the prior art by providing a new device that integrates a Faraday cup and one or more optical elements. In accordance with one embodiment of the present disclosure, an integrated system having an optical element and Faraday cup is provided. The integrated system comprises a Faraday cup device including a Faraday cup electrode configured to be held at a first potential, wherein the Faraday cup device further includes an enclosure having an aperture configured to receive a charged particle beam along an axis. The integrated system also comprises a current measurement device operably coupled to the Faraday cup device, wherein the current measurement device is configured to measure a current of the charged particle beam.

The integrated system also comprises an optical element configured to manipulate light along the charged particle beam axis, and a transparent conductive layer disposed on a part of the optical element interior to the enclosure, wherein the transparent conductive layer is configured to be held at substantially the same potential as the Faraday cup electrode. The part of the optical element having the transparent conductive layer is configured to receive a charged particle beam.

In accordance with another embodiment of the present disclosure, a method is provided for combining the functionalities of a Faraday cup and optical element along the same spatial axis. The method comprises the steps of providing an optical element, and a Faraday cup device, wherein the Faraday cup device includes a Faraday cup electrode and an aperture configured to receive a charged particle beam along an axis. The method also comprises providing a current measurement device operably coupled to the Faraday cup device, coating at least part of the optical element with a transparent conductive layer, and electrically connecting the Faraday cup electrode and the coated at least part of the optical element.

The method also comprises receiving a charged particle beam at the Faraday cup electrode and/or the coated at least part of the optical element.

These, as well as other objects, features and benefits will now become clear from a review of the following detailed description of illustrative embodiments and the accompanying drawings.

DETAILED DESCRIPTION OF THE DISCLOSURE

The integrated optical element and Faraday cup of the present disclosure is designed to resolve incompatibilities between Faraday cups and optical elements. Faraday cups are designed to capture charged particles in a vacuum. Once the charged particle beam is captured, measurements can be taken. An example of one such measurement is a current measurement for the charged particle beam. However, unlike optical elements, Faraday cups are not generally designed to transmit light or manipulate it in any specific way. Thus, optical elements and related applications (such as focusing or imaging) are not enabled on an axis that passes through a Faraday cup.

By contrast, optical elements are generally incapable of measuring charged particle beam currents or transmitting charged particles. Optical elements are generally composed of optically transparent materials, which may be insulating and therefore unsuitable for use with applications involving charged particles. Thus, charged particle beam current measurements are not enabled along the axis of an optical system.

This new integration of a Faraday cup with one or more optical elements combines the functionalities of a Faraday cup and optical element or elements into a single device. The integrated device of the present disclosure has a comparatively smaller footprint in that the integrated device requires less space than the two devices separately. This new integrated device further permits the functionalities of both devices to be enabled simultaneously along the same spatial axis.

The integrated device of the present disclosure is suitable for applications in which optical functionalities, including light manipulation, are desired along an axis passing through a Faraday cup. Because the integrated device may act as a Faraday cup, the integrated device may be used to measure charged particle beam currents.

In addition, the integrated device may be used as a retarding field energy analyzer to measure the energy distribution in a charged particle beam. Such energy distribution analyses may be useful in determining the effects of chromatic aberration in a given ion optical system. One boundary of the Faraday cup may be formed by a lens or other suitable optical elements capable of manipulating light along the axis of the Faraday cup. A transparent conductor may be applied to the surface of the optical element interior to the cup. This transparent conductive layer facilitates the simultaneous functions of taking charged particle beam current measurements, analyzing the retarding field energy in a charged particle beam, and manipulating light.

Figure 1A:
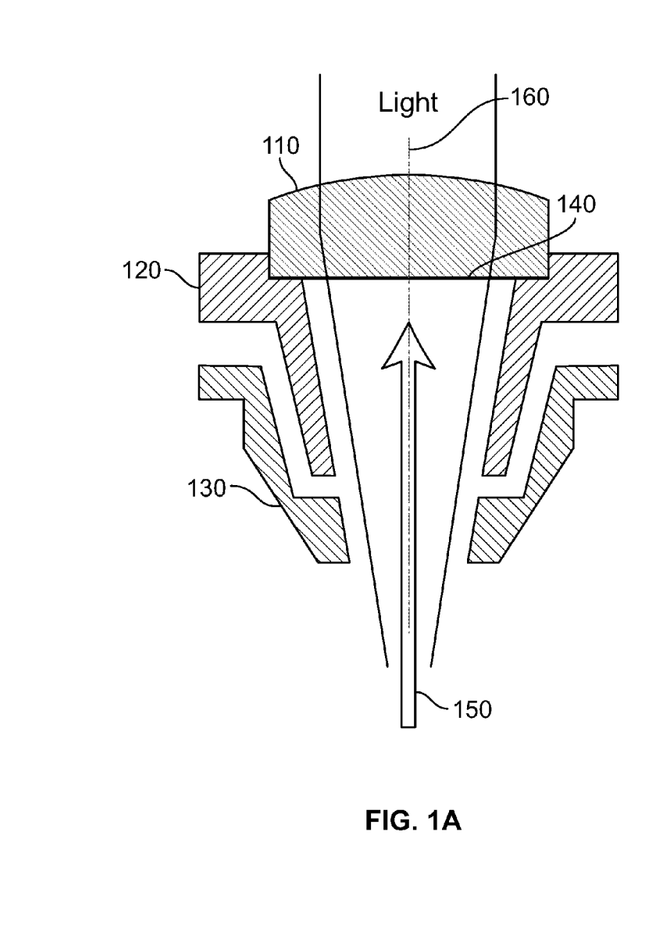
Fig. 1A is a cross-section view of a device that includes an integrated optical objective and Faraday cup in accordance with one embodiment of the present disclosure.

Referring now to FIG. 1A, illustrated is a cross-section view of a device that includes an integrated optical objective and Faraday cup in accordance with one embodiment of the present disclosure. As shown in FIG. 1A, enclosure 100 has a conical interior and a contoured exterior. Enclosure 100 houses four main components. These components are the optical objective/element 110, the Faraday cup electrode 120, the segmented suppressor/blanker/retarder electrode 130 and a transparent conductive layer 140. The enclosure 100 is similar to a Faraday cup structure in that it is a conductive metallic enclosure having an aperture through which a charged particle beam 150 can be received by the enclosure 100 along axial symmetry line 160 of enclosure 100.

The optical element in the embodiment of FIG. 1A is a fused-silica aspheric lens 110. Although the embodiment of FIG. 1A is a lens 110, it should be understood that the optical element could be any number of optical elements or optical systems, including systems having one or more lenses, windows, beamsplitters, Fourier Transform infrared (FTIR) spectrometers, mirrors, prisms, spheres and wedges, or any other optical element or system that is capable of being coated and interfaced with the Faraday cup. Even a simple glass plate may be sufficient to serve as an optical element.

Lens 110 can be used to manipulate light along axis 160. For example, lens 110 may be used for imaging, laser-beam focusing, and other applications incorporating light manipulation. A transparent conductive layer 140, such as a layer of indium tin oxide, covers and coats the flat side of lens 110. The transparent conductive layer 140 need only coat the portion of the optical element onto which the charged particle beam will pass.

It may be desirable to electrically couple the transparent conductive layer 140 to the Faraday cup electrode 120. Accordingly, the coated side of lens 110 may be electrically coupled to, or situated against, the Faraday cup electrode 120 in order to form the flat side of the conical enclosure 100. In this manner, the coated side of lens 110 will be held at the same electric potential as the Faraday cup electrode 120.

The conical enclosure 100 is conductive on all parts of the interior and forms the Faraday cup that enables measurement of charged particle beam current. A charged particle beam 150 along axis 160 is incident on the interior of the enclosure 100, and may be collected by the conductive cup enclosure 100.

A measurable current may be created by these charged particles since the Faraday electrode 120 is part of an electronic circuit. It is often desirable that the current detected by a Faraday cup truly represent the current of detected charged particles. Accordingly, it may be desirable to stop secondary electrons from being emitted from the Faraday cup. The suppressor/blanker/retarder electrode 130 of FIG. 1A is configured to remove unwanted current signals that can result from secondary electrons produced when the charged particle beam impinges on an electrode surface.

The suppressor/blanker/retarder electrode 130 near the open aperture of the enclosure 100 may be used to confine secondary electrons to a region within the enclosure 100 so that secondary electrons can be re-captured by the interior of enclosure 100. Secondary electrons may be emitted from an electrode's surface when an energetic beam of charged particles strikes the surface of the electrode. If the secondary electrons are not collected by the interior of enclosure 100, spurious currents may be induced in the circuit designed to measure the current of the incident beam.

Figure 1B:
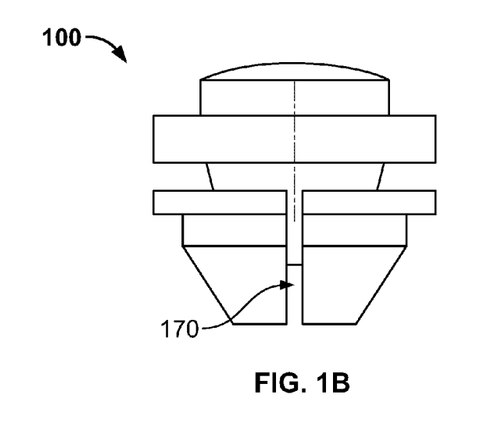
FIG. 1B is a front view of the enclosure of FIG. 1A.
Figure 1C:
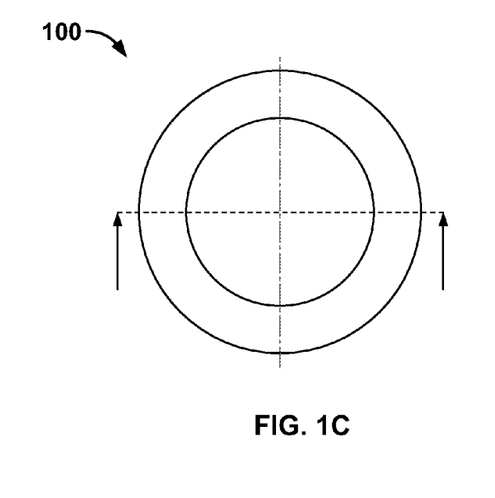
FIG. 1C is a top view of the enclosure of FIG. 1A.

If desired, the suppressor/blanker electrode 130 may be segmented into parts to allow deflection of the ion beam as it enters the Faraday cup electrode 120. Referring now to FIG. 1B, illustrated is a front view of the enclosure 100 of FIG. 1A. Segmentation line 170 shows where the two halves of the suppressor/blanker electrode may be segmented. Referring now to FIG. 1C, illustrated is a top view of the enclosure 100 of FIG. 1A.

Figure 2:
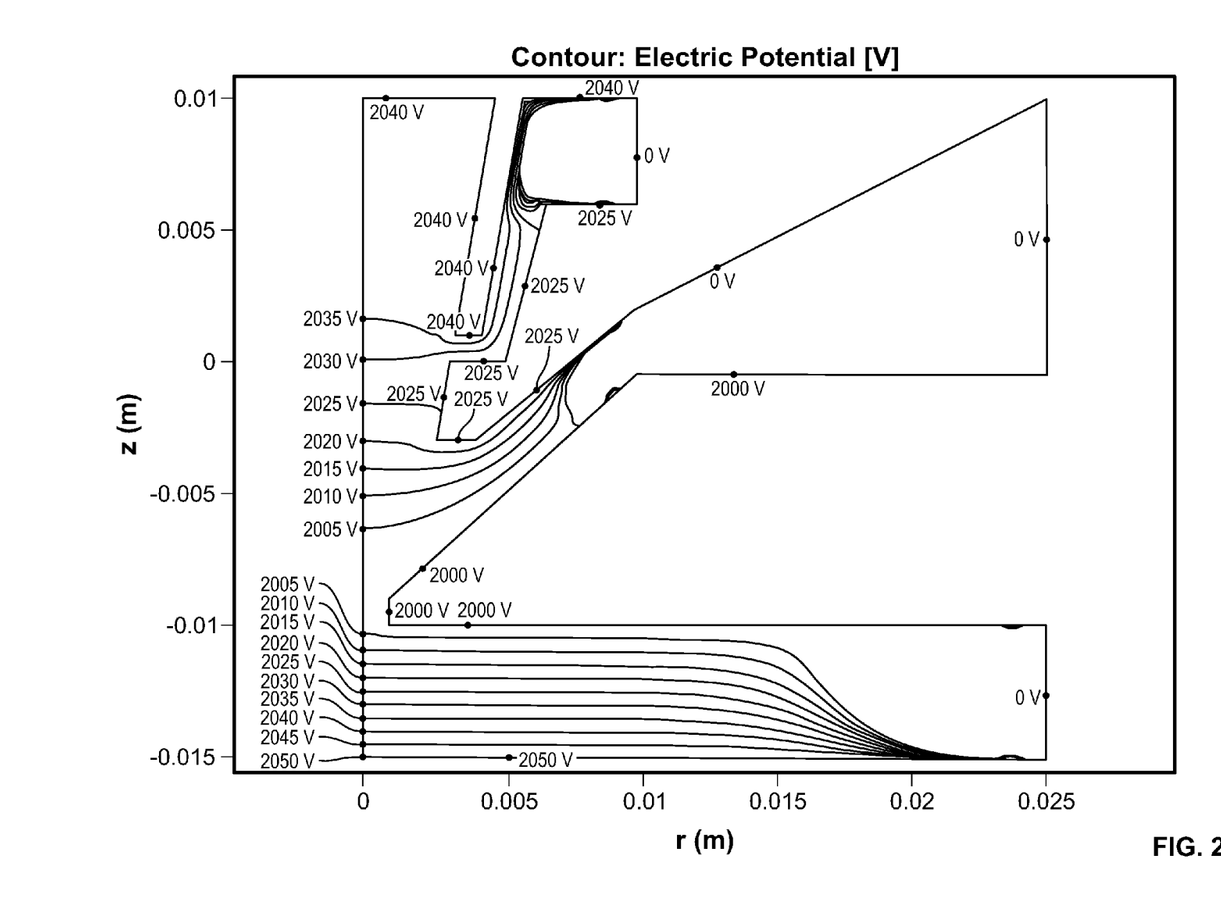
FIG. 2 is a graphical illustration of electric potential for the area inside of a Faraday cup device in accordance with one embodiment of the present disclosure.

Referring now to FIG. 2, illustrated is the electric potential for a typical charged particle beam current measurement application. The electric potential map for an area inside the Faraday cup device of FIG. 1A is axially symmetric about a central axis ($r=0$ meters (m)) for the specified electrode voltages. The Faraday cup is shown with another accelerating electrode configured to increase the velocity of electrons or ions. The accelerating electrode may have been a part of the apparatus that was the source of the charged particle beam. An example of such an apparatus is a magneto-optical trap based ion source (MOTIS). The use of the accelerating electrode is representative of a typical application.

The charged particle beam source has potentials on its lower electrode surfaces of 2050 V and 2000 V. These potentials are appropriate for accelerating positively charged particles at the location $z=-0.15$ m, $r=0$ m, into the Faraday cup. In addition, the potentials may be appropriate for accelerating positively charged particles at the location $r=0.001$ m and $z$ ranges from $-0.015$ m and $0.01$ m. These accelerated particles may strike the Faraday cup electrode, which is held at a potential of 2040 V, creating a measurable current. It should be noted that these currents can be quite small. A picoammeter may be suitable for measuring such small currents.

The collision of the positively charged particles with the electrode surfaces may release secondary electrons. The secondary electrons may be created at a potential of 2040 V and may have a distribution of energies with the majority of them having less than 10 eV of energy. In order to prevent the secondary electrons from escaping the Faraday cup, the suppressor voltage can be set (in this example 2025 V) to create a potential which traps the electrons in the cup. It should be noted that, in lieu of a suppressor/blanker/retarder electrode, other suppression techniques are known in the art and may be used. For example, magnetic fields may be used for suppression. Also by way of example, a very small aperture hole may be used to receive the charged particle beam; this type of design has also been used for secondary electron suppression.

Figure 3:
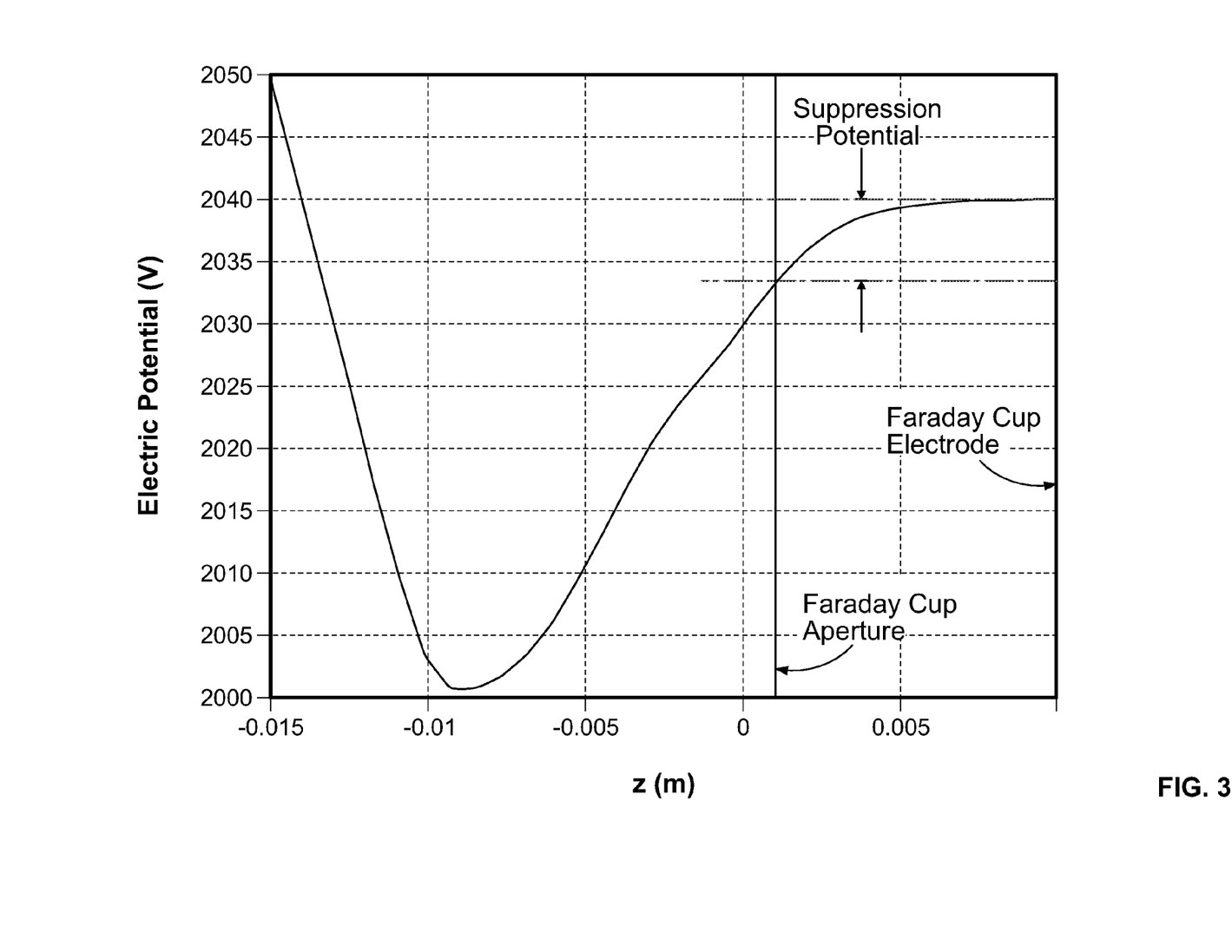
FIG. 3 is a graphical illustration of electric potential along the axis of symmetry of a Faraday cup in accordance with one embodiment of the present disclosure.

Referring now to FIG. 3, illustrated is the potential on axis ($r=0$ m) for the electrode configuration shown in FIG. 2. The operation of the suppression electrode can be seen in this Figure. The suppression electrode prevents secondary electrons, produced by the collision of the measured charged particle beam with the Faraday cup electrode, from escaping the Faraday cup and introducing spurious current signals.

The difference between the potential at the Faraday cup aperture and the potential at the electrode defines a so-called suppression potential. Secondary electrons created at the Faraday cup electrode having an energy less than the suppressor potential may not have sufficient energy to escape the region inside the Faraday cup and would be re-collected by the suppressor electrode. Accordingly, spurious currents resulting from uncollected secondary electrons can be effectively eradicated by applying an appropriate voltage to the suppressor electrode.

The integrated device of the present disclosure is suitable for applications in which optical access and manipulation of light is desired along an axis passing through a Faraday cup, as in an application that incorporates use of a magneto optical trap-based ion source (MOTIS).

The integration of the Faraday cup device and optical element makes it possible to simultaneously measure beam current, analyze longitudinal beam energy spread, and manipulate light along the same spatial axis.

Figure 4:
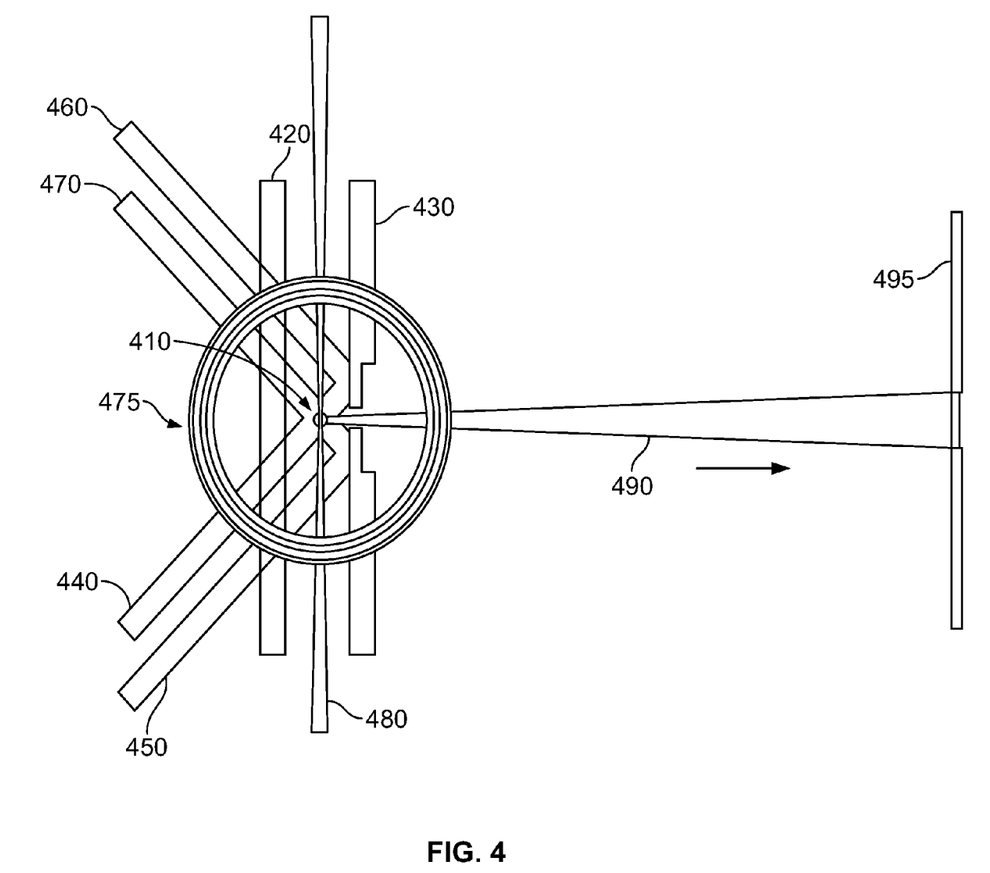
FIG. 4 is a schematic of a magneto-optical trap-based ion source used to provide a charged particle beam in accordance with one embodiment of the present disclosure.

Referring now to FIG. 4, illustrated is a MOTIS that can be used to propagate a charged particle beam to the integrated device of the present disclosure. A magneto-optical trap (MOT) 410 is created between two electrodes 420, 430. Electrode 430 has a mirrored surface. Electrode 420 has a fused silica optical flat with a transparent conductive coating. The MOT includes six laser beams, four of which are shown. These four laser beams 440, 450, 460, 470 reflect from the mirrored electrode 430 as shown. Another pair of MOT beams (not shown) would enter the MOT on a plane that is perpendicular to the drawing page. The magnetic field of the MOT is generated by coil pair 475. An ionization laser 480 may traverse the MOT 410 so that ions are produced and removed through an aperture in electrode 430. The ion beam 490 propagates in a predetermined direction, and may be detected with an image intensifier 495 as shown. Alternatively, the ion beam 490 may be configured to propagate toward an enclosure that includes the integrated optical element and Faraday cup of the present disclosure.

Figure 5:
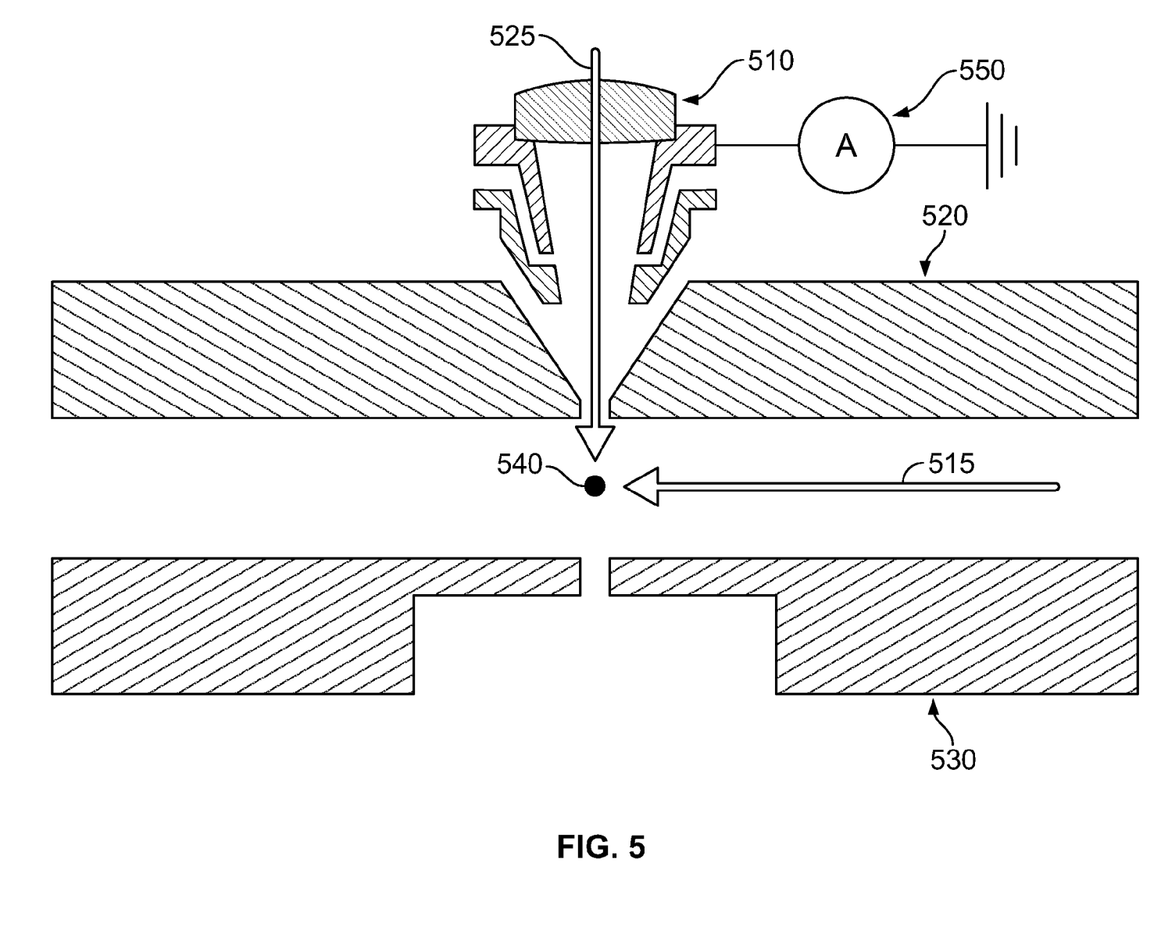
FIG. 5 is a cross-section view of an integrated optical objective and Faraday cup as used with a magneto-optical trap-based ion source in accordance with one embodiment of the present disclosure.

Referring now to FIG. 5, illustrated is a cross-section view of an integrated optical objective and Faraday cup as used with a MOTIS in accordance with one embodiment of the present disclosure. The integrated optical objective and Faraday cup 510 is shown situated above an upper electrode 520 (also called an upper accelerating electrode or top plate) and lower electrode 530 (also called a bottom plate). The charged particle source in a MOTIS is a laser-cooled group of atoms known as a magneto-optical trap (MOT) 540. Atoms in the MOT 540 may be photo-ionized by horizontal laser beam 515 and/or vertical laser beam 525 to create charged particles in the MOTIS. These charged particles include ions and electrons, and may be extracted from the location of the MOT along on axis defined by an applied electric field.

Along this axis, ions may be emitted in an opposite direction relative to the electrons. Charged particle current may also be measured from this axis. Recognizing that there is a one-to-one correspondence between the number of electrons and ions produced in a MOTIS, the ion beam current can be determined by measuring the electron beam current, allowing runtime monitoring of the ion beam current without interrupting its operation. This capability can also be used to generate a control signal for feedback to enhance beam current stability. Also shown in FIG. 5 is a picoammeter 550 used to measure the charged particle beam current. As shown, the picoammeter 550 is connected in series with the integrated device 510 and ground. It should also be understood that the picoammeter need not be connected in series with the integrated device 510 and ground. The picoammeter or other measuring device could be operably coupled to the integrated devices in a number of different configurations which are known in the art.

The axis defined by the electric field is convenient not only for measuring charged particle currents and measuring retarding field energy, it is also convenient for high numerical aperture optical imaging of the MOT. In addition, by focusing the photo-ionization laser along this axis, the MOTIS can be operated in a potentially useful high-current mode. All of these functionalities are simultaneously enabled by this invention in a simple and compact way.

Figure 6:
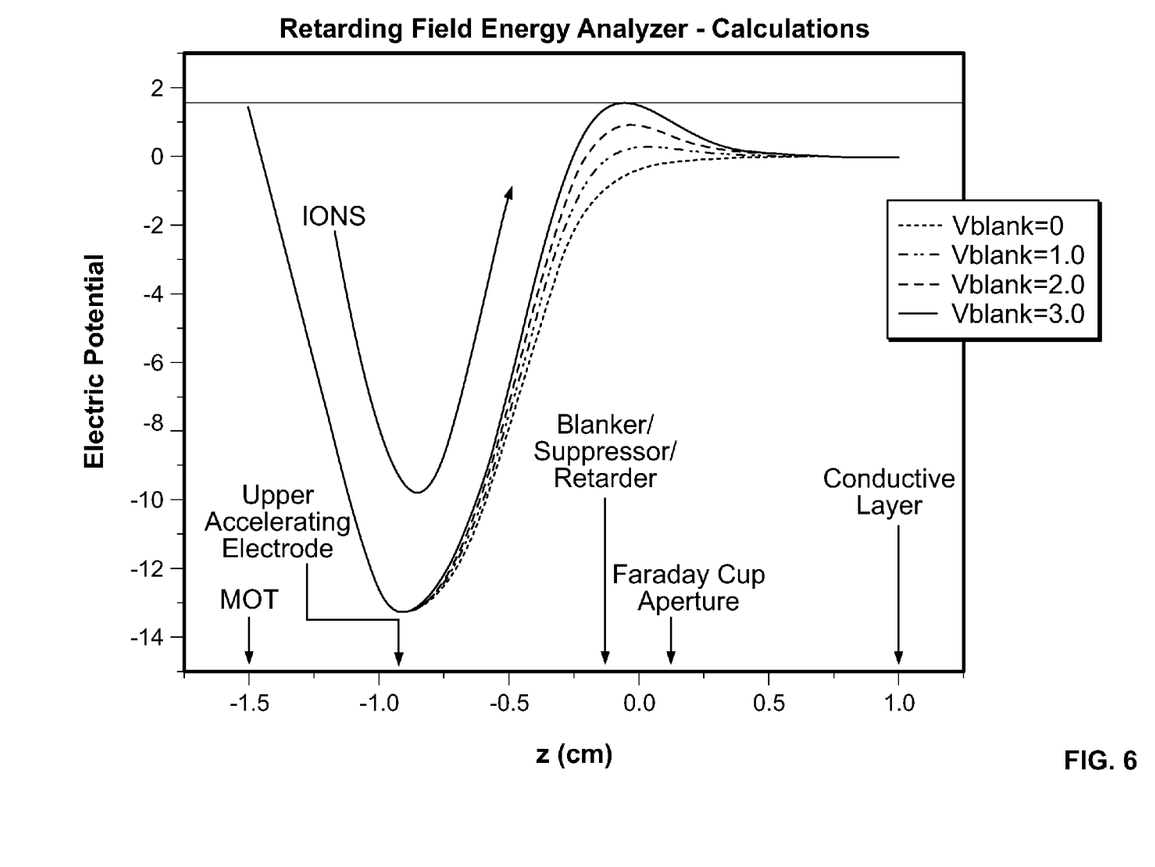
FIG. 6 illustrates electric potentials appropriate for a measurement analyzing the energy spread in an incident charged particle beam in accordance with one embodiment of the present disclosure.

Referring now to FIG. 6, illustrated are electric potentials appropriate for a measurement analyzing the energy spread in an incident charged particle beam in accordance with one embodiment of the present disclosure. In this example, ions are created at the MOT location at a potential of −1.5 V. (Voltage may be negative for electrons/negative ions or positive for positive ions.) The ions may be accelerated in the positive z direction between the MOT and upper accelerating electrode which is held at a potential of −13.2 V.

The curves in the graph of FIG. 6 give potentials governing the trajectory of the ions in the z-direction for various voltages applied to the suppressor/blanker/retarder electrode. The suppressor voltages in the graph of FIG. 6 are, moving from the bottom curve to the top curve, 0 V, 1.0 V, 2.0 V and 3.0 V, respectively. As the voltage on the suppressor/blanker/retarder electrode increases, the height of the potential barrier for entry into the Faraday cup (held at a potential of 0 V) also increases. When the suppressor/blanker/retarder voltage is 3 V, ions created at 1.5 V no longer have enough energy to enter the Faraday cup and instead are redirected (near z=−0.2 cm) and begin moving in the negative z direction.

In practice, the ion beam will have or acquire an energy distribution, with some particles having above average energy and some having below average energy. Thus, the precise potential applied to the suppressor/blanker electrode at which these particles are prevented from entering the Faraday cup may differ amongst the charged particles. That is, the suppression will likely also have a distribution of energy.

Figure 7:
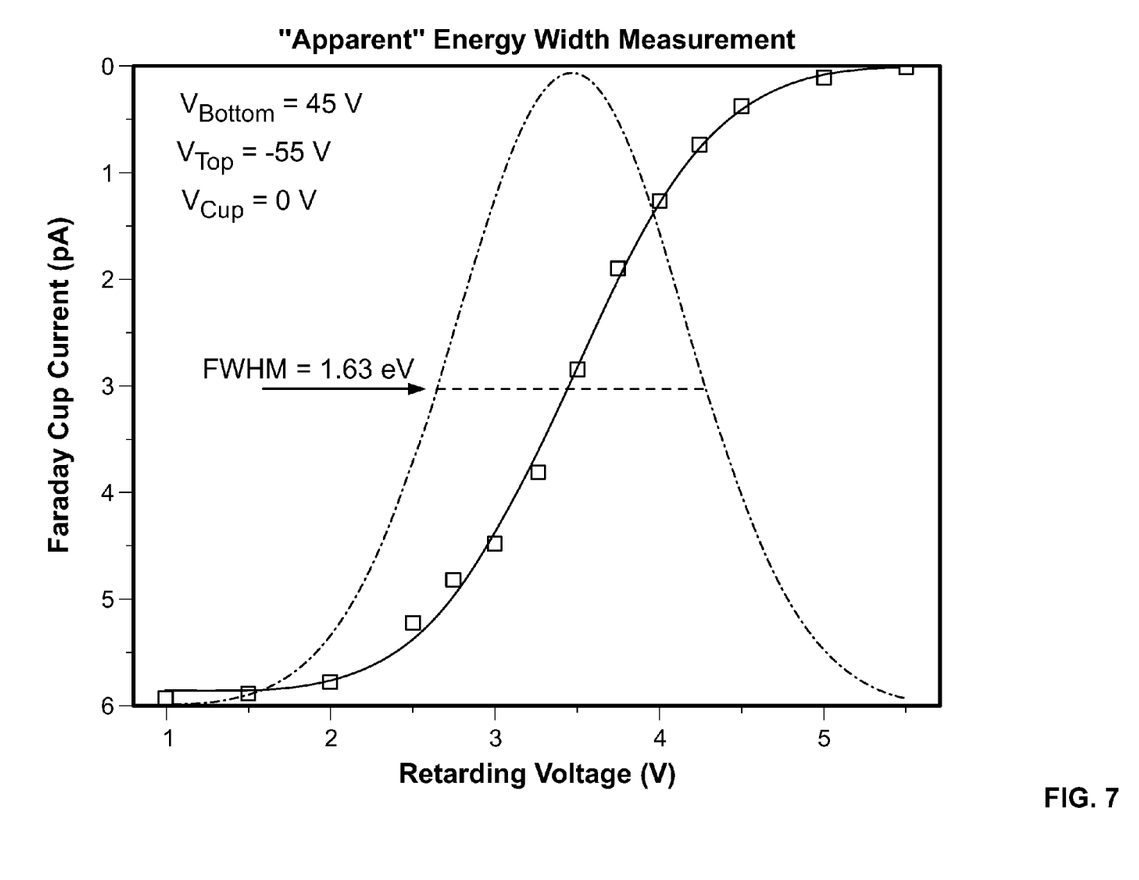
FIG. 7 illustrates an example of the apparent energy spread of an incident beam using the retarding field analysis described in connection with FIG. 6.

Referring now to FIG. 7, illustrated is an example of the apparent energy spread of an incident beam using the retarding field analysis described in FIG. 6. On the y axis, the measured current decreases moving upward along the axis from about 60 picoamperes toward 0 V. When the suppressor/retarder voltage is low, the measured current is maximal as illustrated by the line with black squares.

When voltages are high, the measured current is zero. At intermediate voltages, e.g., between 2 V and 5 V, a fraction of the total current is measured, which corresponds to the integral of all ions which have more than the required energy for entering the Faraday cup. The derivative of the measured current is proportional to the energy distribution, from which the energy spread can be determined full width at half maximum (FWHM).

While the specification describes particular embodiments of the present invention, those of ordinary skill can devise variations of the present invention without departing from the inventive concept.

We claim:

1. An integrated system having an optical element and Faraday cup, the system comprising:
   a Faraday cup device including a Faraday cup electrode configured to be held at a first potential, wherein the Faraday cup device further includes an enclosure having an aperture configured to receive a charged particle beam along an axis;
   a current measurement device operably coupled to the Faraday cup device, wherein the current measurement device is configured to measure a current of the charged particle beam;
   an optical element configured to manipulate light along the charged particle beam axis;
   a transparent conductive layer disposed on a part of the optical element interior to the enclosure, wherein the transparent conductive layer is configured to be held at substantially the same potential as the Faraday cup electrode, and
   wherein said part of the optical element having the transparent conductive layer is configured to receive a charged particle beam.

2. The system of claim 1, further comprising:
   a suppressor/blanker electrode disposed within the Faraday cup enclosure, wherein the suppressor/blanker electrode is configured to suppress the outflow of secondary electrons from the Faraday cup enclosure.

3. The system of claim 2, wherein the Faraday cup device is further configured to measure the longitudinal energy spread of the charged particle beam.

4. The system of claim 2, wherein the suppressor electrode is segmented into substantially equal halves, thus permitting deflection of an ion beam as it enters the Faraday cup electrode.

5. The system of claim 1, wherein the transparent conductive layer is composed of indium tin oxide.

6. The system of claim 1, further comprising:
   a magneto-optical trap-based ion source configured to provide a charged particle beam.

7. The system of claim 1, wherein the current measurement device is a picoammeter.

8. The system of claim 1, wherein the optical element is a lens, window, beamsplitter, Fourier Transform infrared (FTIR) spectrometer, mirror, prism, sphere or wedge.

9. A method for combining the functionalities of a Faraday cup and optical element along the same spatial axis, comprising the steps of:
   providing an optical element configured to manipulate light along an axis
   providing a Faraday cup device, wherein the Faraday cup device includes a Faraday cup electrode and an aperture configured to receive a charged particle beam along the axis;
   providing a current measurement device operably coupled to the Faraday cup device;
   coating at least part of the optical element with a transparent conductive layer;
   electrically connecting the Faraday cup electrode and the coated at least part of the optical element; and
   receiving a charged particle beam at the Faraday cup electrode and/or the coated at least part of the optical element.

10. The method of claim 9, further comprising:
    suppressing the outflow of secondary electrons from the Faraday cup enclosure.

11. The system of claim 10, further comprising:
    analyzing retarding field energy for the charged particle beam.

12. The system of claim 10, wherein the suppressor electrode is segmented into substantially parts, thus permitting deflection of a charged particle beam as it enters the Faraday cup electrode.

13. The method of claim 9, wherein the transparent conductive layer is composed of indium tin oxide.

14. The method of claim 9, wherein the charged particle beam is received from a magneto-optical trap-based ion source.

15. The method of claim 9, wherein the optical element is a lens, window, beamsplitter, Fourier Transform infrared (FTIR) spectrometer, mirror, prism, sphere or wedge.

16. The method of claim 9, further comprising:
measuring the charged particle beam current.

17. The method of claim 9, further comprising:
manipulating light along the charged particle beam axis.

* * * * *